United States Patent [19]
Armstrong et al.

[11] Patent Number: 5,873,897
[45] Date of Patent: Feb. 23, 1999

[54] METHOD AND APPARATUS FOR DUAL CHAMBERED TACHYARRHYTHMIA CLASSIFICATION AND THERAPY

[75] Inventors: Randolph K. Armstrong; D. Curtis Deno; Douglas J. Cook, all of Missouri City; Dat H. Truong, Houston, all of Tex.

[73] Assignee: Sulzer Intermedics Inc., Angleton, Tex.

[21] Appl. No.: 934,361

[22] Filed: Sep. 19, 1997

[51] Int. Cl.$^6$ .................................................. A61N 5/00
[52] U.S. Cl. ............................................................ 607/14
[58] Field of Search ...................................... 607/9, 14, 5

[56] References Cited

U.S. PATENT DOCUMENTS

| | | |
|---|---|---|
| 5,086,772 | 2/1992 | Larnard et al. . |
| 5,350,406 | 9/1994 | Nitzsche et al. ........................ 607/14 |
| 5,383,910 | 1/1995 | den Dulk . |
| 5,411,530 | 5/1995 | Akhtar . |

OTHER PUBLICATIONS

Lavergne et al., "Initial Clinical Experience with the First Dual–Chamber Implantable Cardioverter Defibrillator" PACE 19: 656, 1996.

Matula et al., "Analysis of Tachyarrhythmia Type from Stored Electrograms in ICD Devices using Mathematical Modeling", PACE 19: 614 (1996).

ELA Medical, "Defender 9001 User's Manual" 1995.

Gillberg et al., "Automatic Detection of Atrial Tachyarrhythmias for an Implantable Dual Chamber Defibrillator", PACE 19: 625, 1996.

Carpentier et al., "Differentiation of Sinus Tachycardia from Ventricular Tachycardia", PACE 9: 1063–1068 (1968).

Wood et al, "Comparison of Bipolar Atrial Electrogram Amplitude in Sinus Rhythm, Atrial Fibrillation, and Atrial Flutter", PACE 19: 150–156 (1996).

Leong et al., "MATIC–An Intracardiac Tachycardia Classification System", PACE 15: 1317–1331 (1992).

Li et al. "Ventriculoatrial Conduction in Patients with Implantable Cardioverter Defibrillators", PACE 17: 2304–2306, 1994.

Leenhardt et al., Detection of the Atrial Activity by a New Dual Chamber Implantable Cardioverter Defibrillator, PACE 19: 582, 1996.

Mabo et al., "A New Algorithm Using Dual–Chamber Detection for Arrhythmia Classification in Automatic Implantable Cardioverter–Defibrillator", PACE, 19: 583 (1996).

C.A. Walsh et al., "Differentiation of Arrhythmias in the Dog by Measurement of Activation Sequence Using an Atrial and Two Ventricular Electrodes", PACE 11: 1732–1738 (1988).

Alberola et al., "RR Interval Variability in Irregular Monomorphic Ventricular Tachycardia and Atrial Fibrillation", Circulation, 93: 295–300 (1995).

Arzbaecher et al., "Automatic Tachycardia Recognition", PACE 541–547 (1984).

Jenkins et al., "A single Atrial Extrastimulus Can Distinguish Sinus Tachycardia", PACE 9: 1063–1068 (1988.

*Primary Examiner*—Scott M. Getzow
*Attorney, Agent, or Firm*—John R. Merkling

[57] ABSTRACT

A method and apparatus for classifying and treating tachyarrhythmias. A cardiac stimulator includes an algorithm that uses dual chamber sensing to determine the type of tachyarrhythmia detected. If the tachyarrhythmia is of a type that responds well to ventricular therapy, such as a tachyarrhythmia originating in the ventricle rather than the atrium, the tachyarrhythmia is grouped into a treatable category. Accordingly, the cardiac stimulator applies therapy, or therapies, to the ventricle to remedy the ventricular tachyarrhythmia.

39 Claims, 3 Drawing Sheets

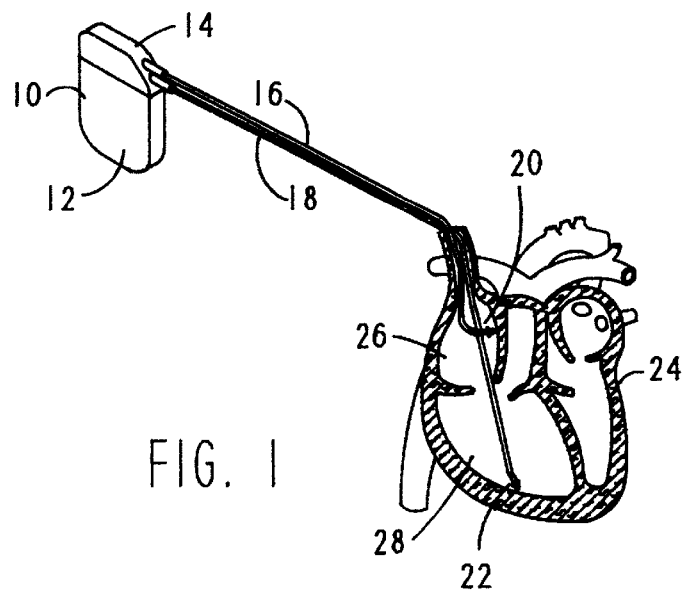
FIG. 1
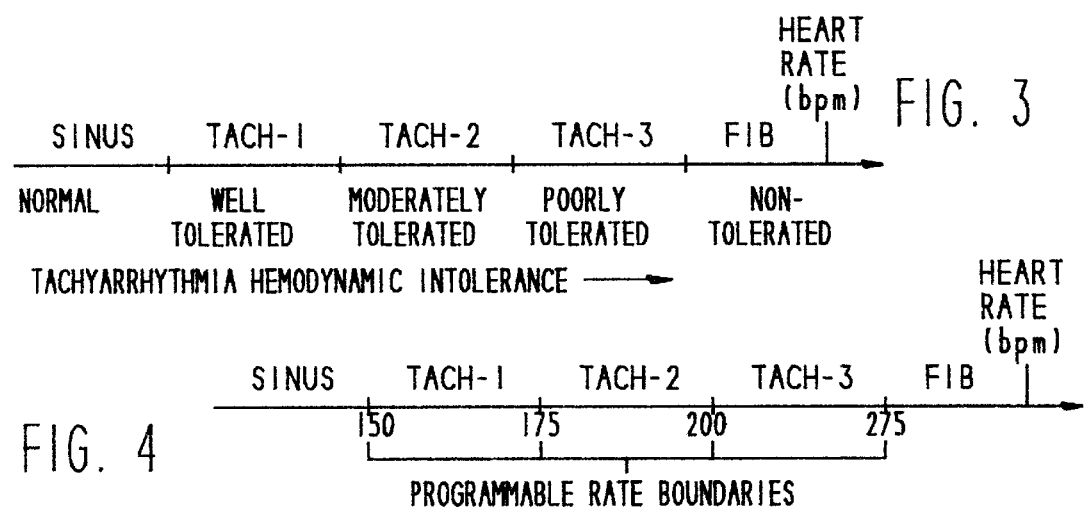
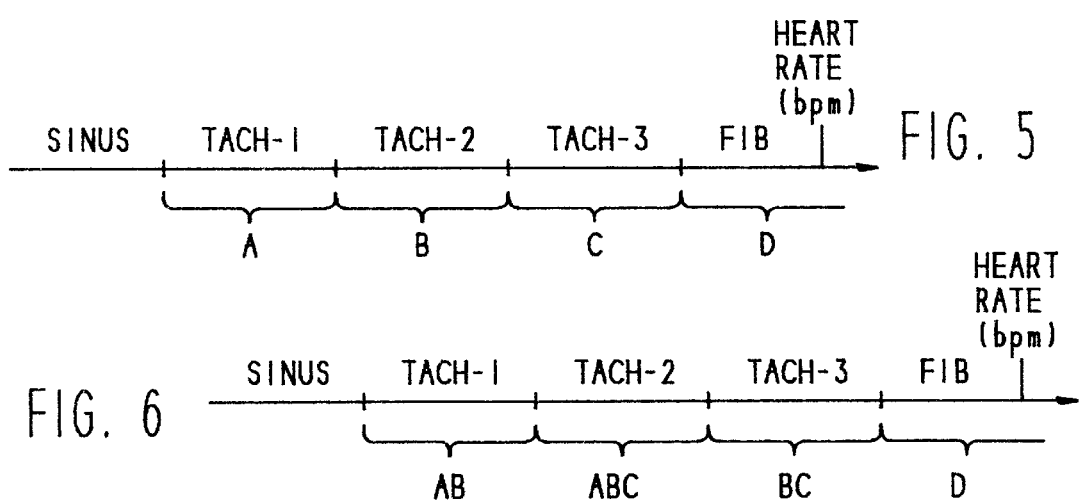

METHOD AND APPARATUS FOR DUAL CHAMBERED TACHYARRHYTHMIA CLASSIFICATION AND THERAPY

BACKGROUND OF THE INVENTION

1. Field Of The Invention

The present invention relates generally to cardiac stimulators and, more particularly, to cardiac stimulators having the ability to classify and treat tachyarrhythmias.

2. Description Of The Related Art

As most people are aware, the human heart is an organ having four chambers. A septum divides the heart in half, with each half having two chambers. The upper chambers are referred to as the left and right atria, and the lower chambers are referred to as the left and right ventricles. Deoxygenated blood enters the right atrium through the pulmonary veins. Contraction of the right atrium and of the right ventricle pump the deoxygenated blood through the pulmonary arteries to the lungs where the blood is oxygenated. This oxygenated blood is carried to the left atrium by the pulmonary veins. From this cavity, the oxygenated blood passes to the left ventricle and is pumped to a large artery, the aorta, which delivers the pure blood to the other portions of the body through the various branches of the vascular system.

In the normal human heart, the sinus node (generally located near the junction of the superior vena cava and the right atrium) constitutes the primary natural pacemaker by which rhythmic electrical excitation is developed. The cardiac impulse arising from the sinus node is transmitted to the two atrial chambers. In response to this excitation, the atria contract, pumping blood from those chambers into the respective ventricles. The impulse is transmitted to the ventricles through the atrioventricular (AV) node to cause the ventricles to contract. This action is repeated in a rhythmic cardiac cycle in which the atrial and ventricular chambers alternately contract and pump, then relax and fill. One-way valves between the atrial and ventricular chambers in the right and left sides of the heart and at the exits of the right and left ventricles prevent backflow of the blood as it moves through the heart and the circulatory system.

The sinus node is spontaneously rhythmic, and the cardiac rhythm originating from the sinus node is referred to as sinus rhythm. This capacity to produce spontaneous cardiac impulses is called rhythmicity. Some other cardiac tissues also possess this electrophysiologic property and, hence, constitute secondary natural pacemakers. However, the sinus node is the primary pacemaker because it has the fastest spontaneous rate and because the secondary pacemakers tend to be inhibited by the more rapid rate at which impulses are generated by the sinus node.

The resting rates at which sinus rhythm occurs in normal people differ from age group to age group, generally ranging between 110 and 150 beats per minute ("bpm") at birth, and gradually slowing in childhood to the range between 65 and 85 bpm usually found in adults. The resting sinus rate, typically referred to simply as the "sinus rate," varies from one person to another and, despite the aforementioned usual adult range, is generally considered to lie anywhere between 60 and 100 bpm (the "sinus rate range") for the adult population.

A number of factors may affect the sinus rate, and some of those factors may slow or accelerate the rate sufficiently to take it outside of the sinus rate range. Slow rates (below 60 bpm) are referred to as sinus bradycardia, and high rates (above 100 bpm) are referred to as sinus tachycardia. In particular, sinus tachycardia observed in healthy people arises from various factors which may include physical or emotional stress, such as exercise or excitement, consumption of beverages containing alcohol or caffeine, cigarette smoking, and the ingestion of certain drugs. The sinus tachycardia rate usually ranges between 101 and 160 bpm in adults, but has been observed at rates up to (and in infrequent instances, exceeding) 200 bpm in younger persons during strenuous exercise.

Sinus tachycardia is sometimes categorized as a cardiac arrhythmia, since it is a variation from the normal sinus rate range. Arrhythmia rates which exceed the upper end of the sinus rate range are termed tachyarrhythmias. Healthy people usually experience a gradual return to their normal sinus rate after the removal of the factors giving rise to sinus tachycardia. However, people suffering from disease may experience abnormal arrhythmias that may require special, and in some instances immediate, treatment. In this text, we typically refer to abnormally high rates that have not yet been determined to be caused by myocardial malfunction as tachycardias and to abnormally high rates that have been determined to be caused by myocardial malfunction as tachyarrhythmias.

It should also be appreciated that an abnormal tachyarrhythmia may initiate fibrillation. Fibrillation is a tachyarrhythmia characterized by the commencement of completely uncoordinated random contractions by sections of conductive cardiac tissue of the affected chamber, quickly resulting in a complete loss of synchronous contraction of the overall mass of tissue and a consequent loss of the blood-pumping capability of that chamber.

In addition to rhythmicity, other electrophysiologic properties of the heart include excitability and conductivity. Excitability, which is the property of cardiac tissue to respond to a stimulus, varies with the different periods of the cardiac cycle. As one example, the cardiac tissue is not able to respond to a stimulus during the absolute refractory phase of the refractory period, which is approximately the interval of contraction from the start of the QRS complex to the commencement of the T wave of the electrocardiogram. As another example, the cardiac tissue exhibits a lower than usual response during another portion of the refractory period constituting the initial part of the relative refractory phase, which is coincident with the T wave. Also, the excitability of the various portions of the cardiac tissue differs according to the degree of refractoriness of the tissue.

Similarly, the different portions of the heart vary significantly in conductivity, which is a related electrophysiologic property of cardiac tissue that determines the speed with which cardiac impulses are transmitted. For example, ventricular tissue and atrial tissue are more conductive than AV junction tissue. The longer refractory phase and slower conductivity of the AV junction tissue give it a significant natural protective function, as described in more detail later.

For a variety of reasons, a person's heart may not function properly and, thus, endanger the person's well-being. Most typically, heart disease affects the rhythmicity of the organ, but it may also affect the excitability and/or conductivity of the cardiac tissue as well. As most people are aware, medical devices have been developed to facilitate heart function in such situations. For instance, if a person's heart does not beat properly, a cardiac stimulator may be used to provide relief. A cardiac stimulator is a medical device that delivers electrical stimulation to a patient's heart. A cardiac stimulator generally includes a pulse generator for creating electrical stimulation pulses and a conductive lead for delivering these electrical stimulation pulses to the designated portion of the heart. As described in more detail below, cardiac stimulators generally supply electrical pulses to the heart to keep the heart beating at a desired rate, although they may supply a relatively larger electrical pulse to the heart to help the heart recover from fibrillation.

Early pacemakers were devised to treat bradycardia. These pacemakers did not monitor the condition of the heart. Rather, early pacemakers simply provided stimulation pulses at a fixed rate and, thus, kept the heart beating at that fixed rate. However, it was found that pacemakers of this type used an inordinate amount of energy due to the constant pulse production. Even the sinus node of a heart in need of a pacemaker often provides suitable rhythmic stimulation occasionally. Accordingly, if a heart, even for a short period, is able to beat on its own, providing an electrical stimulation pulse using a pacemaker wastes the pacemaker's energy.

To address this problem, pacemakers were subsequently designed to monitor the heart and to provide stimulation pulses only when necessary. These pacemakers were referred to as "demand" pacemakers because they provided stimulation only when the heart demanded stimulation. If a demand pacemaker detected a natural heartbeat within a prescribed period of time, typically referred to as the "escape interval", the pacemaker provided no stimulation pulse. Because monitoring uses much less power than generating stimulation pulses, the demand pacemakers took a large step toward conserving the limited energy contained in the pacemaker's battery.

Clearly, the evolution of the pacemaker did not cease with the advent of monitoring capability. Indeed, the complexity of pacemakers has continued to increase in order to address the physiological needs of patients as well as the efficiency, longevity, and reliability of the pacemaker. For instance, even the early demand pacemakers provided stimulation pulses, when needed, at a fixed rate, such as 70 pulses per minute. To provide a more physiological response, pacemakers having a programmably selectable rate were developed. So long as the heart was beating above this programmably selected rate, the pacemaker did not provide any stimulation pulses. However, if the heart rate fell below this programmably selected rate, the pacemaker sensed the condition and provided stimulation pulses as appropriate.

To provide even further physiological accuracy, pacemakers have now been developed that automatically change the rate at which the pacemaker provides stimulation pulses. These pacemakers are commonly referred to as "rate-responsive" pacemakers. Rate-responsive pacemakers sense a physiological parameter of the patient and alter the rate at which the stimulation pulses are provided to the heart. Typically, this monitored physiological parameter relates to the changing physiological needs of the patient. For instance, when a person is at rest, the person's heart need only beat relatively slowly to accommodate the person's physiological needs. Conversely, when a person is exercising, the person's heart tends to beat rather quickly to accommodate the person's heightened physiological needs.

Unfortunately, the heart of a person in need of a pacemaker may not be able to beat faster on its own. Prior to the development of rate-responsive pacemakers, patients were typically advised to avoid undue exercise, and pacemaker patients that engaged in exercise tended to tire quickly. Rate-responsive pacemakers help relieve this constraint by sensing one or more physiological parameters of a patient that indicates whether the heart should be beating slower or faster. If the pacemaker determines that the heart should be beating faster, the pacemaker adjusts its base rate upward to provide a faster pacing rate if the patient's heart is unable to beat faster on its own. Similarly, if the pacemaker determines that the patient's heart should be beating more slowly, the pacemaker adjusts its base rate downward to conserve energy and to conform the patient's heartbeat with the patient's less active state.

As noted above, pacemakers have historically been employed primarily for the treatment of heart rates which are unusually slow, referred to as bradyarrhythmias. However, over the past several years cardiac pacing has found significantly increasing usage in the management of heart rates which are unusually fast, referred to as tachyarrhythmias. Anti-tachyarrhythmia pacemakers take advantage of the previously mentioned inhibitory mechanism that acts on the secondary natural pacemakers to prevent their spontaneous rhymicity, sometimes termed "postdrive inhibition" or "overdrive inhibition". In essence, the heart may be stimulated with a faster than normal pacing rate (1) to suppress premature atrial or ventricular contractions that might otherwise initiate ventricular tachycardia, flutter (a tachyarrhythmia exceeding 200 bpm), or fibrillation or (2) to terminate an existing tachyarrhythmia.

Typically, these pulses need only be of sufficient magnitude to stimulate the excitable myocardial tissue in the immediate vicinity of the pacing electrode. However, another technique for terminating tachyarrhythmias, referred to as cardioversion, utilizes apparatus to shock the heart synchronized to the tachyarrhythmia with one or more current or voltage pulses of considerably higher energy content than that of the pacing pulses. Defibrillation, a related technique, also involves applying one or more high energy "countershocks" to the heart in an effort to overwhelm the chaotic contractions of individual tissue sections to allow reestablishment of an organized spreading of action potential from cell to cell of the myocardium and, thus, restore the synchronized contraction of the mass of tissue.

In the great majority of cases, atrial fibrillation is hemodynamically tolerated and not life-threatening because the atria provide only a relatively small portion (typically on the order of 15 to 20 percent) of the total volume of blood pumped by the heart per unit time, typically referred to as cardiac output. During atrial fibrillation, the atrial tissue remains healthy because it is continuing to receive a fresh supply of oxygenated blood as a result of the continued pumping action of the ventricles. Atrial tachyarrhythmia may also be hemodynamically tolerated because of the natural protective property of the AV junctional tissue attributable to its longer refractory period and slower conductivity than atrial tissue. This property renders the AV junctional tissue unable to respond fully to the more rapid atrial contractions. As a result, the ventricle may miss every other, or perhaps two of every three, contractions in the high rate atrial sequence, resulting in 2:1 or 3:1 A-V conduction and, thus, maintain relatively strong cardiac output and an almost normal rhythm.

Nevertheless, in cases where the patient is symptomatic or at high risk in events of atrial tachyarrhythmia or fibrillation, special treatment of these atrial disorders may be appropriate. Such circumstances may include, for example, instances where the patient suffers from ventricular heart disease and cannot easily withstand even the small consequent reduction of ventricular pumping capability, as well as instances where the rapid atrial rhythm is responsible for an excessively rapid ventricular rate. The methods of treatment commonly prescribed by physicians for treating atrial tachyarrhythmia and fibrillation include medication, catheter ablation, pacing therapy, cardiac shock therapy, and in some cases, surgically creating an A-V block and implanting a ventricular pacemaker.

In contrast to the atrial arrhythmias discussed above, cardiac output may be considerably diminished during an episode of ventricular tachyarrhythmia because the main pumping chambers of the heart, the ventricles, are only partially filled between the rapid contractions of those chambers. Moreover, ventricular tachyarrhythmia can present a risk of acceleration of the arrhythmia into ventricular fibrillation. As in the case atrial fibrillation, ventricular fibrillation is characterized by rapid, chaotic electrical and mechanical activity of the excitable myocardial tissue. However, in contrast to atrial fibrillation, ventricular fibrillation manifests an instantaneous cessation of cardiac output as the result of the ineffectual quivering of the ventricles-a condition that typically requires almost immediate treatment.

Conventional cardiac stimulators monitor the ventricular rate to determine the nature of an arrhythmia. When a ventricular tachyarrhythmia is detected, the cardiac stimulator delivers anti-tachyarrhythmia pacing therapy to the ventricle or a higher level shock to the ventricle. However, the information obtained by solely monitoring the ventricular rate can be misleading. For example, in some cases a sinus tachycardia caused by exercise could be misinterpreted as a ventricular tachyarrhythmia. Clearly, in this situation the therapy described above is not needed. At best, the delivery of such therapy reduces the longevity of the cardiac stimulator and causes unwanted disruption of the patient's activity. Also, atrial tachyarrhythmias can cause ventricular tachyarrhythmias. The delivery of the therapy described above to the ventricle in such a circumstance does not relieve the atrial tachyarrhythmia. Thus, the longevity of the cardiac stimulator will be needlessly reduced.

Physicians may tolerate the occasional misinterpretation of this type, along with the delivery of unnecessary therapy, if the physician determines that it is in the patient's best interest to treat even questionable ventricular tachycardias. Of course, such a decision creates a situation afflicted by the disadvantages discussed above. Alternatively, physicians may raise the threshold rate or otherwise alter the criterion used by the cardiac stimulator for detecting tachyarrhythmias. Although this decision may avoid some of the disadvantages discussed above, the cardiac stimulator may fail to treat relatively mild tachyarrhythmias that occur at rates below the raised threshold.

The present invention is directed to addressing one or more of the problems set forth above.

SUMMARY OF THE INVENTION

In accordance with one aspect of the present invention, there is provided a cardiac stimulator for classifying and treating tachyarrhythmias. The cardiac stimulator includes an atrial sensing circuit adapted to deliver an atrial signal correlative to a condition of an atrium of a heart, and a ventricular sensing circuit adapted to deliver a ventricular signal correlative to a condition of a ventricle of the heart. A pulse generator is adapted to deliver electrical stimulation to the ventricle. A control circuit is coupled to the atrial sensing circuit to receive the atrial signal and coupled to the ventricular sensing circuit to receive the ventricular signal. The control circuit classifies the ventricular tachyarrhythmia into a treatable category or an untreatable category based on an evaluation of the interval between the atrial signal and the ventricular signal. The control circuit directs the pulse generator to deliver electrical stimulation to the ventricle in response to detecting and classifying a ventricular tachyarrhythmia only in the treatable category.

In accordance with another aspect of the present invention, there is provided a cardiac stimulator. The cardiac stimulator includes an atrial sensing circuit adapted to deliver an atrial signal correlative to atrial events occurring in an atrium of a heart, and a ventricular sensing circuit adapted to deliver a ventricular signal correlative to ventricular events occurring in a ventricle of the heart. A pulse generator is adapted to deliver electrical stimulation to the ventricle. A control circuit executes an algorithm for controlling the control circuit. The control circuit is coupled to the atrial sensing circuit to receive the atrial signal and coupled to the ventricular sensing circuit to receive the ventricular signal. The algorithm performs the actions of: determining an interval between ventricular events; determining whether the interval between ventricular events indicates a ventricular tachyarrhythmia; if the interval between ventricular events indicates a ventricular tachyarrhythmia, determining whether an interval between atrial events and ventricular events is stable; if the interval between atrial events and ventricular events is not stable, determining whether the interval between ventricular events is stable; if the interval between ventricular events is stable, directing the control circuit to direct the pulse generator to deliver electrical stimulation to the ventricle; if the interval between ventricular events is not stable, withholding treatment of the ventricular tachyarrhythmia; if the interval between atrial events and ventricular events is stable, determining whether the interval between atrial events and ventricular events is normal; if the interval between atrial events and ventricular events is normal, withholding treatment of the ventricular tachyarrhythmia; if the interval between atrial events and ventricular events is not normal, comparing a frequency of atrial events with a frequency of ventricular events; if the frequency of atrial events is greater than the frequency of ventricular events, withholding treatment of the ventricular tachyarrhythmia; and if the frequency of atrial events is not greater than the frequency of ventricular events, directing the control circuit to direct the pulse generator to deliver electrical stimulation to the ventricle.

In accordance with still another aspect of the present invention, there is provided a cardiac stimulator. The cardiac stimulator includes: means for determining whether a ventricular tachyarrhythmia exists; means for evaluating an interval between atrial events and ventricular events to place each existing ventricular tachyarrhythmia into a treatable category or an untreatable category; means for treating each existing ventricular tachyarrhythmia that is placed in the treatable category; and means for withholding treatment of each existing ventricular tachyarrhythmia that is placed in the untreatable category.

In accordance with yet another aspect of the present invention, there is provided a computer algorithm that comprises the steps of: determining an interval between ventricular events; determining whether the interval between ventricular events indicates a ventricular tachyarrhythmia; if the interval between ventricular events indicates a ventricular tachyarrhythmia, determining whether an interval between atrial events and ventricular events is stable; if the interval between atrial events and ventricular events is not stable, determining whether the interval between ventricular events is stable; if the interval between ventricular events is stable, treating the ventricular tachyarrhythmia; if the interval between ventricular events is not stable, withholding treatment of the ventricular tachyarrhythmia; if the interval between atrial events and ventricular events is stable, determining whether the interval between atrial events and ventricular events is normal; if the interval between atrial events and ventricular events is normal, withholding treatment of the ventricular tachyarrhythmia; if the interval between atrial events and ventricular events is not normal, comparing a number of atrial events in a given time with a number of ventricular events in the given time; if the number of atrial events in the given time is greater than the number of ventricular events in the given time, withholding treatment of the ventricular tachyarrhythmia; and if the number of atrial events in the given time is not greater than the number of ventricular events in the given time, treating the ventricular tachyarrhythmia.

In accordance with a further aspect of the present invention, there is provided a cardiac stimulator that includes: means for determining an interval between ventricular events; means for determining whether the interval between ventricular events indicates a ventricular tachyarrhythmia; means for determining whether an interval between atrial events and ventricular events is stable if the interval between ventricular events indicates a ventricular tachyarrhythmia; means for determining whether the interval between ventricular events is stable if the interval between atrial events and ventricular events is not stable; means for treating the ventricular tachyarrhythmia if the interval between ventricular events is stable; means for withholding treatment of the ventricular tachyarrhythmia if the interval between ventricular events is not stable; means for determining whether the interval between atrial events and ventricular events is normal if the interval between atrial events and ventricular events is stable; means for withholding treatment of the ventricular tachyarrhythmia if the interval between atrial events and ventricular events is normal; means for comparing a frequency of atrial events with a frequency of ventricular events if the interval between atrial events and ventricular events is not normal; means for withholding treatment of the ventricular tachyarrhythmia if the frequency of atrial events is greater than the frequency of ventricular events; and means for treating the ventricular tachyarrhythmia if the frequency of atrial events is not greater than the frequency of ventricular events.

In accordance with an even further aspect of the present invention, there is provided a method of classifying tachyarrhythmias that includes the steps of: (a) determining whether a ventricular tachyarrhythmia exists; (b) evaluating an interval between atrial events and ventricular events to place each existing ventricular tachyarrhythmia in one of a plurality of categories.

In accordance with a still further aspect of the present invention, there is provided a method of classifying and treating tachyarrhythmias that includes the steps of: (a) determining whether a ventricular tachyarrhythmia exists; (b) evaluating an interval between atrial events and ventricular events to place each existing ventricular tachyarrhythmia into a treatable category or an untreatable category; (c) treating each existing ventricular tachyarrhythmia that is placed in the treatable category; and (d) withholding treatment of each existing ventricular tachyarrhythmia that is placed in the untreatable category.

In accordance with a yet further aspect of the present invention, there is provided a method of classifying and treating tachyarrhythmias that includes the steps of: (a) determining whether a tachyarrhythmia exists in a ventricle; (b) categorizing each existing tachyarrhythmia based on a likelihood of the existing tachyarrhythmia being remedied by electrically stimulating the ventricle; and (c) electrically stimulating the ventricle to treat only each existing tachyarrhythmia that is likely to be remedied by electrically stimulating the ventricle.

In accordance with another aspect of the present invention, there is provided a method of classifying and treating tachyarrhythmias that includes the steps of: (a) sensing ventricular events and atrial events of a heart; (b) determining whether a ventricular tachyarrhythmia exists based on the ventricular events; (c) determining whether an existing ventricular tachyarrhythmia is caused by the atrial events or by the ventricular events; (d) treating the existing ventricular tachyarrhythmia if caused by the ventricular events; and (e) withholding treatment if the existing ventricular tachyarrhythmia if caused by the atrial events.

In accordance with still another aspect of the present invention, there is provided a method of classifying and treating tachyarrhythmias that includes the steps of: (a) determining an interval between ventricular events; (b) determining whether the interval between ventricular events indicates a ventricular tachyarrhythmia; (c) determining whether an interval between atrial events and ventricular events is stable if the interval between ventricular events indicates a ventricular tachyarrhythmia; (d) determining whether the interval between ventricular events is stable if the interval between atrial events and ventricular events is not stable; (e) treating the ventricular tachyarrhythmia if the interval between ventricular events is stable; (f) withholding treatment of the ventricular tachyarrhythmia if the interval between ventricular events is not stable; (g) determining whether the interval between atrial events and ventricular events is normal if the interval between atrial events and ventricular events is stable; (h) withholding treatment of the ventricular tachyarrhythmia if the interval between atrial events and ventricular events is normal; (i) comparing a number of atrial events in a given time with a number of ventricular events in the given time if the interval between atrial events and ventricular events is not normal; (j) withholding treatment of the ventricular tachyarrhythmia if the number of atrial events in the given time is greater than the number of ventricular events in the given time; and (k) treating the ventricular tachyarrhythmia if the number of atrial events in the given time is not greater than the number of ventricular events in the given time.

BRIEF DESCRIPTION OF THE DRAWINGS

The foregoing and other advantages of the invention will become apparent upon reading the following detailed description and upon reference to the drawings in which:

FIG. 1 illustrates a cardiac stimulator having two leads coupled to a patient's heart;

FIG. 3 illustrates a diagram of a heart rate spectrum that is partitioned into various arrhythmia classes with associated hemodynamic tolerance;

FIG. 4 illustrates a diagram of a heart rate spectrum that illustrates programmable rates at the boundaries of each arrhythmia class;

FIG. 5 illustrates a diagram of a heart rate spectrum that illustrates the assignment of exemplary therapy regimens to the arrhythmia classes;

FIG. 6 illustrates a diagram of a heart rate spectrum that illustrates the assignment of multiple exemplary therapy regimens to the arrhythmia classes.

DESCRIPTION OF SPECIFIC EMBODIMENTS

Figure 2:
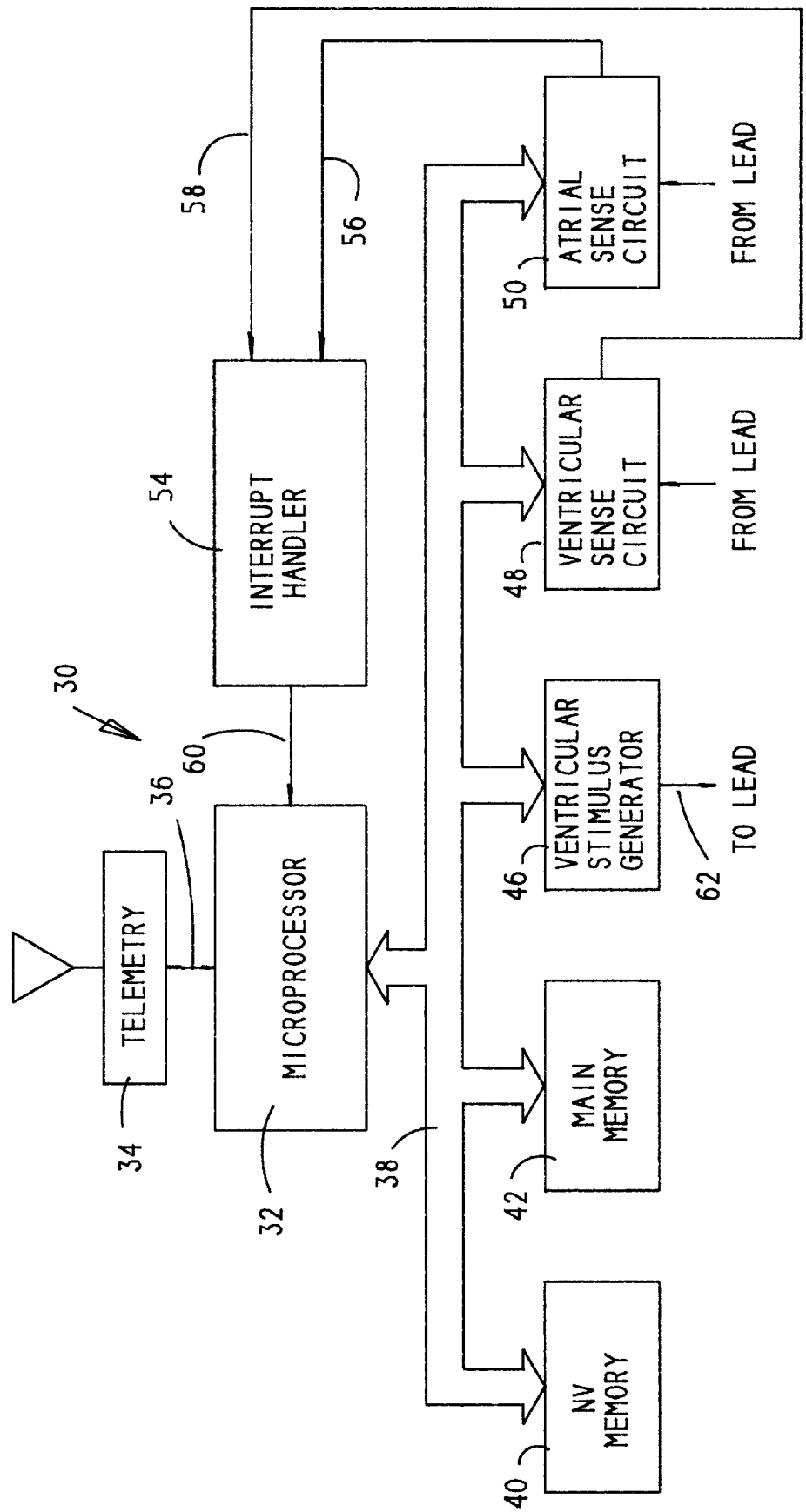
FIG. 2 illustrates a block diagram of one embodiment of a cardiac stimulator's circuitry in accordance with the present invention.

Turning now to the drawings and referring initially to FIG. 1, one embodiment of a cardiac stimulator is illustrated and generally designated by a reference numeral 10. The cardiac stimulator 10 includes an apparatus for classifying and treating tachyarrhythmias that will be described in detail herein. If the cardiac stimulator 10 detects a circumstance that may indicate a tachyarrhythmia, it can determine whether a ventricular tachyarrhythmia exists, determine the cause of the tachyarrhythmia and classify the type of tachyarrhythmia, and, if classified in certain categories as a treatable tachyarrhythmia, treat the tachyarrhythmia.

The body of the cardiac stimulator 10 includes a case 12 and a header 14. The cardiac stimulator 10 may be implantable or non-implantable. If implantable, the case 12 and the header 14 are hermetically sealed to prevent bodily fluids from damaging the internal circuitry of the cardiac stimulator 10. Typically, the case 12 is made of titanium, and the header 14 is made of polyethylene.

In the described embodiment, the cardiac stimulator 10 is a dual chamber cardioverter/defibrillator (ICD), although it should be understood that the teachings set forth herein may apply to other types of cardiac stimulators. Because the cardiac stimulator 10 is a dual chamber ICD, it includes an atrial lead 16 and a ventricular lead 18. Typically, the leads 16 and 18 are generally flexible and include an electrically conductive core surrounded by a protective sheath. For instance, the internal core may be a coiled DFT wire, and the protective sheath may be a coating of polyurethone. One preferred lead is a Thinline (™) lead available from the assignee.

Each lead 16 and 18 includes a respective tip 20 and 22 that is designed to be implanted or coupled to an interior surface of a chamber of the heart 24. As illustrated, the tip 20 of the atrial lead 16 is implanted in an inner wall of the right atrium 26 of the heart 24 for sensing and/or stimulating the right atrium 26. Similarly, the tip 22 of the ventricular lead 18 is implanted in an inner wall of the right ventricle 28 of the heart 24 for sensing and/or stimulating the right ventricle 28.

The cardiac stimulator 10 uses electronic circuitry to perform its functions, such as the circuitry illustrated in FIG. 2 and generally designated by the reference numeral 30. The circuitry 30 includes a microprocessor 32 that controls many functions of the cardiac stimulator 10. A telemetry circuit 34 facilitates communication between the cardiac stimulator 10 and a programmer (not shown) located external to the patient's body. Using the programmer, a physician may program various parameters into the circuitry 30 to tailor the pacemaker's functionality to a patient's particular situation. The telemetry circuitry 34 is coupled to the microprocessor 32 via a bus 36.

To control the functions of the cardiac stimulator 10, the microprocessor 32 is coupled to a variety of other circuits via an address/data bus 38. In this embodiment, for instance, the address/data bus 38 couples the microprocessor 32 to a non-volatile memory, such as the electrically erasable programmable read only memory (EEPROM) 40, a main memory 42, a ventricular stimulus generator 46, a ventricular sense circuit 48, and an atrial sense circuit 50.

A cardiac stimulator may stimulate the heart 24 in both the atrium 26 and the ventricle 28. However, in this embodiment, the cardiac stimulator 10 does not treat atrial arrhythmias because atrial arrhythmias, as discussed previously, tend to be less problematic than ventricular arrhythmias. The atrial lead 20 delivers information on the electrical condition of the atrium 26 to the atrial sense circuit 50. Similarly, the ventricular lead 22 delivers information on the electrical condition of the ventricle 28 to the ventricular sense circuit 48. The atrial sense circuit 50 and the ventricular sense circuit 48 deliver this information to an interrupt handler 54 via lines 56 and 58, respectively. The interrupt handler 54 passes this information to the microprocessor 32 via line 60.

Based, in part, on the information delivered to it by the atrial sense circuit 50 and the ventricular sense circuit 48, the microprocessor 32 controls the ventricular stimulus generator 46. More specifically, the microprocessor 32 controls not only the timing of the stimulation pulse delivered by the ventricular stimulus generator 46 over line 62 to the ventricular lead 22, but it also controls the type, duration, polarity, and amplitude of the stimulation pulse. The microprocessor 32 may also base its control of the ventricular stimulus generator 46 on other parameters, such as information received from other sensors. For example, an activity sensor 64, such as an implanted accelerometer, may be used to gather information relating to changing environmental or physiological conditions.

The type of therapy delivered by the cardiac stimulator 10 may vary depending upon the type of arrhythmia detected. U.S. Pat. No. 4,830,006, issued May 16, 1989, to Haluska et al., the entirety of which is hereby incorporated by reference, discloses that various types of therapies may be applied to the ventricle by a cardiac stimulator depending upon the severity of the detected tachyarrhythmia. This patent describes these types of therapies in great detail, and it is not deemed necessary to repeat such disclosure here. However, a better understanding of the present cardiac stimulator 10 may be gained by a brief overview of these therapies, because the present cardiac stimulator 10 may use these therapies to treat various classifications of tachyarrhythmias.

With reference now to FIG. 3, the heart rate spectrum is partitioned into a multiplicity of regions defining contiguous, successive heart rate ranges. At the lower end of the illustrated heart rate spectrum is sinus rhythm, which is designated SINUS. As the heart rate rises along the spectrum, the spectrum enters progressively higher rate ranges associated with ventricular tachyarrhythmia, respectively labeled TACH-1, TACH-2, and TACH-3. Beyond the ventricular tachycardia ranges of the spectrum lies the range associated with ventricular fibrillation, which is labeled FIB.

It will be observed from FIG. 3 that the spectrum is partitioned such that the rate ranges are representative of respective degrees of hemodynamic tolerance of the patient to cardiac rates in those regions. Generally speaking, heart rates in the SINUS region are normal, whereas rates in the FIB region cannot be tolerated. Furthermore, the ascending order of the three ventricular tachyarrhythmia regions TACH-1, TACH-2, and TACH-3 depicts well tolerated, moderately tolerated, and poorly tolerated classes of tachycardia, respectively. Although three tachyarrhythmia classes are utilized in the present embodiment, the actual number of such classes may be greater or fewer depending on the judgment of the physician regarding the management of arrhythmias and the prescription of therapy regimens for a particular patient, as will become clear from the discussion of therapy considerations below.

The rate ranges of the tachyarrhythmia classes may be selectively designated by assigning specific rate numbers to the boundaries of those regions. For example, the boundary between the SINUS and TACH-1 regions may be set at 150 bpm, the boundary between the TACH-1 and TACH-2 regions may be set at 175 bpm, the boundary between the TACH-2 and TACH-3 regions may be set at 200, and the boundary between the TACH-3 and FIB regions may be set at 275 bpm, as illustrated in FIG. 4. Using the previously mentioned external programmer, each boundary rate may be selectively adjustable by the physician during the programming or reprogramming of the cardiac stimulator 10 based on the particular patient's needs. These programmed boundary rates are stored in one of the memories 40 or 42 associated with the microprocessor 32.

In addition to allowing the physician to designate the boundary rates for the heart rate spectrum, the cardiac stimulator 10 gives the physician the capability to prescribe any of a plurality of basic therapies for treatment of the arrhythmias, to specify the detailed nature of each of those therapies, to designate the sequence in which the therapies are to be delivered in response to a detected arrhythmia in any of the designated arrhythmia regions, and to select the algorithms for detecting arrhythmias in each region. For example, in one embodiment, any of four basic therapies may be selectively designated to treat respective detected events in each of the four arrhythmia classes TACH-1, TACH-2, TACH-3, and FIB. It should be emphasized that the number of basic therapies may be greater or fewer than the number of arrhythmia classes, and there is no particular significance to the common number of them in this embodiment. It is also important to note that the number and complexity of the basic therapies, and of other stored and/or programmable data functions described herein, are limited from a practical standpoint only (not conceptually) by memory type and capacity in the cardiac stimulator and associated programming unit.

In essence, the basic therapies may be defined in any desired manner using any of the potential therapies that may be delivered by the cardiac stimulator 10. Each of the deliverable therapies may be altered (again, within the practical limitations of the device) in terms of its detailed application to achieve the greatest benefit. Thus, the device gives the physician the capability to alter the deliverable therapies and to define them as the basic therapies for a given situation. The latter may then be assigned separately or in any combination as a plurality of regimens or sequences appropriate for treatment of arrhythmias in the respective designated rate ranges, tailored to the particular patient.

For example, as illustrated in FIG. 5, one definition of the four basic therapies of the present embodiment could be as follows for each of the arrhythmia ranges:

THERAPY-A: non-aggressive pacing bursts;
THERAPY-B: aggressive pacing bursts;
THERAPY-C: cardioverting shocks; and
THERAPY-D: defibrillating shocks.

However, therapies A and B could equally well both be defined as aggressive pacing bursts, differing only in the manner in which such aggressive pacing bursts are defined and/or delivered. As another example, therapies A, B, and C could equally well be defined as cardioverting shocks, again differing only in the manner in which such cardioverting shocks are defined and/or delivered. Also, each of the therapies could be defined in any other manner desired by the physician, limited only by the range of therapies deliverable by the stimulator 10.

These therapies typically become increasingly more aggressive not only with the increasing heart rate, but also with the increasing amount of time that a particular arrhythmia exists without responding adequately to treatment. Thus, as illustrated in FIG. 6, the least aggressive basic therapies are initially applied for a given range of tachyarrhythmia, and a more aggressive therapy is subsequently applied if the initial therapy has not remedied the problem in a certain amount of time. In this example, therapy A is initially applied in the TACH-1 and TACH-2 regions, followed by therapy B if therapy A is not successful. In the TACH-2 region, therapy C may be applied if therapy B is not successful. Similarly, therapy C may follow the unsuccessful application of therapy B in the TACH-3 region.

As stated previously, a more detailed explanation of the possible therapies may be found in U.S. Pat. No. 4,830,006. While these therapies have been found to be quite successful for remedying tachyarrhythmias, it is believed that these therapies, and other therapies for treating tachyarrhythmias and fibrillations, may be applied in a more judicious manner by determining the cause of the sensed tachyarrhythmia. For instance, it should be noted that the cardiac stimulator disclosed in this previous patent does not discriminate between ventricular tachyarrhythmias that are the result of atrial events and ventricular tachyarrhythmias that are the result of other events.

Figure 7:
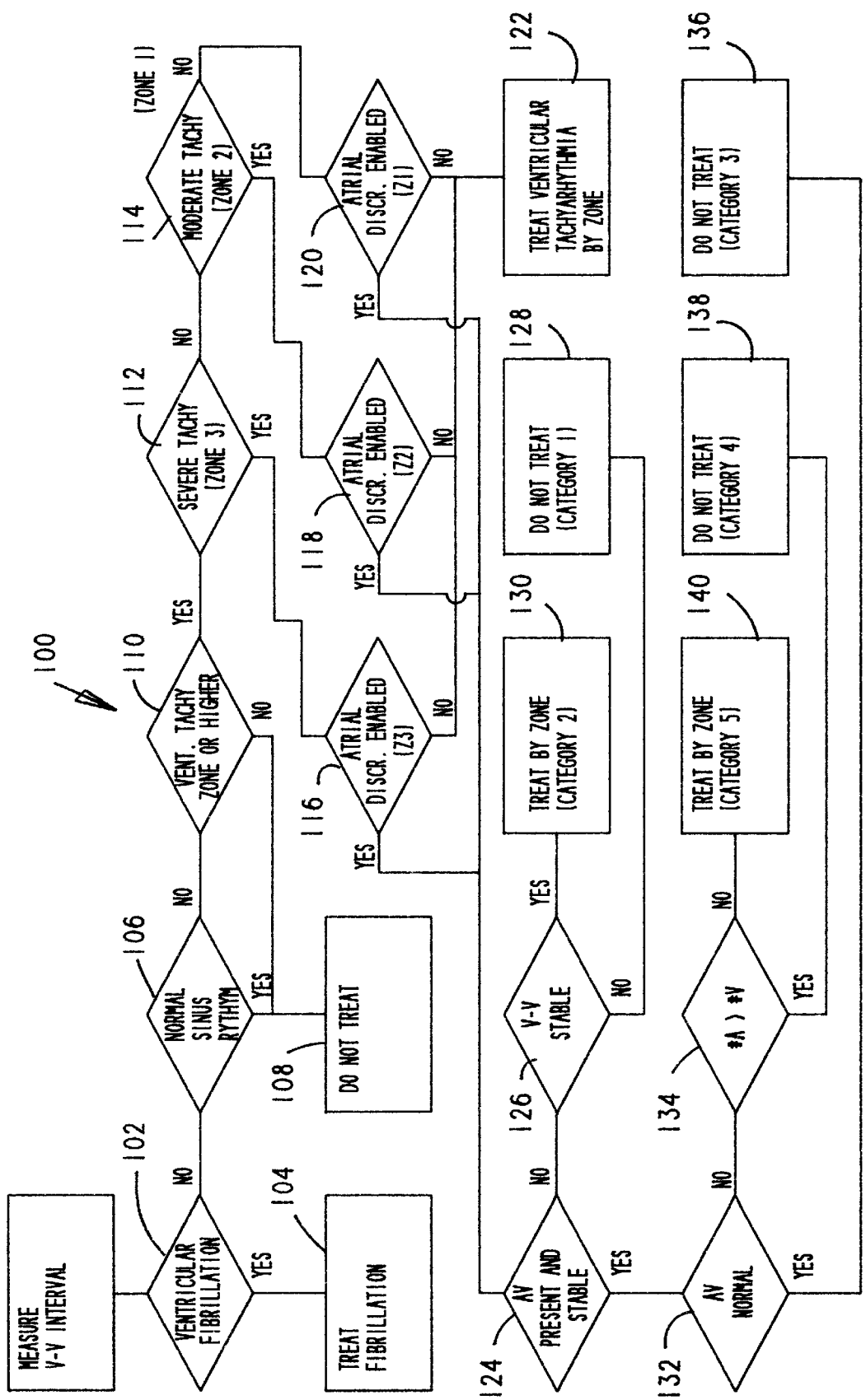
FIG. 7 illustrates a flow chart depicting the functioning of an apparatus and method of classifying tachyarrhythmias and treating them.

FIG. 7 illustrates a flow chart of a method implemented by the cardiac stimulator 10 for detecting a tachyarrhythmia, classifying the detected tachyarrhythmia, and delivering therapy based upon the detection and classification of the tachyarrhythmia. This embodiment is directed toward the detection and classification of treatable ventricular tachyarrhythmias in particular. As a result, the decision branches have been developed to steer the outcome toward the classification of treatable ventricular tachyarrhythmias and non-ventricular arrhythmias. Specifically, the flow chart 100 describes various atrial discrimination methods that are particularly useful in further classifying the tachyarrhythmia in the TACH-1, TACH-2, and TACH-3 regions or zones. As will become apparent from the following description, the atrial discrimination for each of these regions may be selectively enabled or disabled at the physician's discretion. As will be further appreciated from the following description, the atrial discrimination methods classify the detected tachyarrhythmia in each region as tachyarrhythmias that tend to respond well to ventricle stimulation or therapy and as tachyarrhythmias that do not tend to respond well to ventricle stimulation or therapy. Accordingly, with the atrial discrimination enabled, certain types of detected tachyarrhythmias may be classified as not requiring therapy, whereas such detected tachyarrhythmia would have otherwise received therapy if the atrial discrimination method had been disabled.

To determine where the sensed heart rate falls on the heart rate spectrum discussed earlier, the ventricular-to-ventricular (V—V) interval is sensed and evaluated. If the V—V interval is in the FIB portion of the heart rate spectrum, this indicates the presence of ventricular fibrillation. (Block 102). Because a ventricular fibrillation cannot be tolerated, the decision is made to treat the ventricular fibrillation immediately, regardless of its cause. (Block 104). However, if a ventricular fibrillation is not detected, the determination is made as to whether the V—V interval corresponds to a heart rate in the SINUS region of the heart rate spectrum. (Block 106). If the heart rate corresponds to a normal sinus rhythm, no arrhythmia exists so no therapy is applied by the cardiac stimulator 10. (Block 108).

If the heart rate does not fall within either end region of the tachycardia heart rate spectrum, a determination is made as to whether a ventricular tachyarrhythmia exists. (Block 110). If no arrhythmia exists, no therapy is applied. (Block 108). However, if the cardiac stimulator 10 determines that the a ventricular tachyarrhythmia exists, the V—V interval is further evaluated to determine which region or zone, TACH-1, TACH-2, or TACH-3, encompasses the detected heart rate. First, the V—V interval is evaluated to determine whether the heart rate resides in the TACH-3 region of the heart rate spectrum. (Block 112). If not, the V—V interval is evaluated to determine whether the heart rate resides in the TACH-2 region of the heart rate spectrum. (Block 114). If not, the heart rate falls into the TACH-1 region of the heart rate spectrum.

Regardless of which tachyarrhythmia region the heart rate resides in, a determination is made as to whether atrial discrimination method for that particular region is enabled. (Blocks 116, 118, and 120). If the atrial discrimination is not enabled for a particular tachyarrhythmia region, the ventricular tachyarrhythmia is treated according to the particular therapy designated for the particular region, as discussed previously in regard to FIGS. 5 and 6. (Block 122). It should be understood from this portion of the flow chart 100 that the cardiac stimulator 10 advantageously allows a physician to enable or disable the atrial discrimination method for each designated tachyarrhythmia region, TACH-1, TACH-2, or TACH-3. This type of programmability is advantageous because a physician may quite reasonably determine that all severe tachyarrhythmias, for instance, should be treated for a particular patient regardless of the source of such severe tachyarrhythmia, while moderate and mild tachyarrhythmias may be more suitable for selective therapies based on the source of the particular tachyarrhythmia.

If the atrial discrimination feature is enabled for a particular tachyarrhythmia region, the atrial-to-ventricle (A–V) interval is evaluated to determine whether this interval is present and stable. If there is no atrial sense event over the past V—V cycle, the A–V interval is said to be missing, i.e., not present. (Block 124). In this embodiment, the last eight A–V intervals are evaluated. If they do not vary by more than 50 milliseconds, then the interval is determined to be stable. Also, a small number of atrial events, e.g., 2 of 8, may be missing without instability being declared. If the A–V interval is stable, this stability suggests that conduction is taking place between the atrium and the ventricle and, thus, that the atrial event may be responsible for the ventricular event. Accordingly, further steps are taken, as described later, to determine whether atrial events are indeed responsible for the ventricular events.

However, even if the A–V interval is not stable or if many atrial events are missing, atrial activity could still be responsible for the ventricular tachyarrhythmia. To make this determination, the V—V interval is again evaluated to determine whether it is stable. (Block 126). In this embodiment, the last ten V—V intervals are evaluated. If they do not vary by more than 150 milliseconds, then the interval is determined to be stable. If the V—V interval is not stable, this lack of stability suggests that the conduction path between the atrium and the ventricle may not be able to keep up with the rapid pace set in the atrium. Thus, this condition produces an unstable A–V interval even though the ventricular event is being caused by an atrial event. Hemodynamically tolerable atrial tachyarrhythmias that may produce this situation include sinus tachycardia, sinus tachycardia with non-sustained ventricular tachycardia, atrial fibrillation with rapid ventricular conduction, or sinus tachycardia with premature ventricular contractions. In addition, the condition could be a polymorphic ventricular tachycardia with an unstable V—V interval. All of these conditions have been placed in category 1 as conditions which do not require treatment in the form of ventricular therapy. (Block 128).

If, on the other hand, the V—V interval is stable, this suggests that ventricular events are causing the ventricular tachyarrhythmia or that other events that respond to ventricular therapy are causing the ventricular tachyarrhythmia. Accordingly, these events are placed in category 2 and treated. (Block 130). The therapy applied by the cardiac stimulator 10 depends upon whether the sensed ventricular tachyarrhythmia resides in the TACH-1, TACH-2, or TACH-3 region, as discussed with reference to FIGS. 5 and 6. Possible types of tachyarrhythmias which may fall into category 2 include ventricular tachyarrhythmia, polymorphic ventricular tachyarrhythmia, independent ventricular tachyarrhythmia with atrial tachyarrhythmia or atrial fibrillation.

Let us now consider the further evaluations that the cardiac stimulator 10 undertakes if the A–V interval is stable. (Block 124). First, the A–V interval is evaluated to determine whether it is normal. (Block 132). In this embodiment, the last non-missing A–V interval is evaluated to determine if it is in the range of 85 to 300 milliseconds. If so, the A–V interval is determined to be normal. If the A–V interval is normal, this suggests a category of hemologically tolerable tachycardias, most of which are not true ventricular arrhythmias. (Block 134). These conditions, which have been grouped in category 3 and which are not treated, include sinus tachycardia with 1:1, 2:1. . . AV conduction, supraventricular tachycardia with 1:1, 2:1. . . AV conduction, AVNRT, and accessory pathway tachycardia.

If the A–V interval is not normal, the number of atrial events is compared to the number of ventricular events. (Block 136). In this embodiment, the last 32 combined atrial and ventricular events are evaluated to determine this count. If the number atrial events is greater than the number of ventricular events, this indicates that the sensed ventricular tachyarrhythmia is caused by atrial activity, such as atrial fibrillation or atrial flutter with n:1 AV conduction, or SVT with n:1 AV conduction, which are grouped in category 4 and which are not treated. (Block 138). However, if the number of atrial events is not greater than the number of ventricular events, this indicates a condition, either ventricular or non-ventricular in origin, that may be remedied by ventricular therapy. Such conditions, which have been grouped in category 5 and which are treated, include the ventricular events of ventricular tachyarrhythmia with retrograde VA, and polymorphic ventricular tachycardia with retrograde VA. (Block 140).

Although the embodiment discussed above utilizes a cardiac stimulator to categorize and treat the detected ventricular tachyarrhythmias, such a classification technique may be used in various other ways. As one example, treatment may not depend on the classification. Rather, the classification may be determined and stored to be used at a later time by a physician who downloads such information. This information may be useful, for instance, in assisting a physician to diagnose a particular type of heart disease in a patient or in providing the physician with information to program the therapies to be delivered by the cardiac stimulator. In fact, such a classification technique may be used by external diagnostic equipment, rather than a cardiac stimulator, for these same reasons. As another example, the classification technique may be used in conjunction with an automatic external defibrillator. Such a defibrillator may monitor the electrocardiogram of a patient using such a classification technique to determine whether shock therapy is recommended.

Specific embodiments of the invention have been shown by way of example in the drawings and have been described in detail herein. However, the invention may be susceptible to various modifications and alternative forms, and it should be understood that the invention is not intended to be limited to the particular forms disclosed. Rather, the invention is to cover all modifications, equivalents, and alternatives falling within the spirit and scope of the invention as defined by the appended claims.

What is claimed is:

1. A cardiac stimulator for classifying and treating tachyarrhythmias comprising:
    an atrial sensing circuit adapted to deliver an atrial signal correlative to a condition of an atrium of a heart;
    a ventricular sensing circuit adapted to deliver a ventricular signal correlative to a condition of a ventricle of the heart;
    a pulse generator adapted to deliver electrical stimulation to the ventricle; and
    a control circuit coupled to the atrial sensing circuit to receive the atrial signal and coupled to the ventricular sensing circuit to receive the ventricular signal, the control circuit classifying a ventricular tachyarrhythmia into a treatable category or an untreatable category by evaluating an interval between the atrial signal and the ventricular signal to determine the interval's stability, if the interval is stable, determining if an A–V interval is abnormal, the control circuit directing the pulse generator to deliver electrical stimulation to the ventricle if said A–V interval is abnormal.

2. The cardiac stimulator, as set forth in claim 1, wherein the control circuit further classifies the ventricular tachyarrhythmia as one of a mild ventricular tachyarrhythmia, a moderate ventricular tachyarrhythmia, and a severe ventricular tachyarrhythmia.

3. The cardiac stimulator, as set forth in claim 2, wherein the electrical stimulation varies depending upon whether the ventricular tachyarrhythmia is classified as a mild ventricular tachyarrhythmia, a moderate ventricular tachyarrhythmia, or a severe ventricular tachyarrhythmia.

4. The cardiac stimulator, as set forth in claim 1, wherein the control circuit determines the stability of the interval by evaluating a plurality of successive intervals.

5. The cardiac stimulator, as set forth in claim 4, wherein the control circuit determines the interval to be stable if time periods of successive intervals do not vary by more than a given amount.

6. The cardiac stimulator, as set forth in claim 5, wherein the control circuit evaluates the atrial signal to determine whether an atrial event is present between two successive ventricular signals to determine the stability of the interval.

7. The cardiac stimulator, as set forth in claim 6, wherein the control circuit determines the interval to be unstable in response to a given number of absences of an atrial event between successive ventricular signals.

8. The cardiac stimulator, as set forth in claim 1, wherein the control circuit determines that the A–V interval is abnormal if said interval is outside a predetermined range.

9. The cardiac stimulator, as set forth in claim 8, wherein said predetermined range is 85 to 300 milliseconds.

10. The cardiac stimulator, as set forth in claim 1, wherein said control circuit, having determined that the interval is stable and that the A–V interval is abnormal, determines if a number of atrial events exceeds a number of ventricular events during a period, and does not direct the pulse generator to deliver electrical stimulation if the number of atrial events exceeds the number of ventricular events.

11. The cardiac stimulator, as set forth in claim 10, wherein the control circuit determines that the A–V interval is abnormal if said interval is outside a predetermined range.

12. The cardiac stimulator, as set forth in claim 11, wherein said predetermined range is 85 to 300 milliseconds.

13. A cardiac stimulator comprising:
    an atrial sensing circuit adapted to deliver an atrial signal correlative to atrial events occurring in an atrium of a heart;
    a ventricular sensing circuit adapted to deliver a ventricular signal correlative to ventricular events occurring in a ventricle of the heart;
    a pulse generator adapted to deliver electrical stimulation to the ventricle; and
    a control circuit executing an algorithm for controlling the control circuit, the control circuit coupled to the atrial sensing circuit to receive the atrial signal and coupled to the ventricular sensing circuit to receive the ventricular signal, the algorithm:
    determining an interval between ventricular events;
    determining whether the interval between ventricular events indicates a ventricular tachyarrhythmia;
    if the interval between ventricular events indicates a ventricular tachyarrhythmia, determining whether an interval between atrial events and ventricular events is stable;
    if the interval between atrial events and ventricular events is stable, determining whether the interval between atrial events and ventricular events is normal;
    if the interval between atrial events and ventricular events is normal, withholding treatment of the ventricular tachyarrhythmia;
    if the interval between atrial events and ventricular events is not normal, comparing a relative frequency of atrial events and ventricular events;
    if the frequency of atrial events is greater than the frequency of ventricular events, withholding treatment of the ventricular tachyarrhythmia; and
    if the frequency of atrial events is not greater than the frequency of ventricular events, directing the control circuit to direct the pulse generator to deliver electrical stimulation to the ventricle.

14. The cardiac stimulator, as set forth in claim 13, wherein the algorithm further classifies the ventricular tachyarrhythmia as one of a mild ventricular tachyarrhythmia, a moderate ventricular tachyarrhythmia, and a severe ventricular tachyarrhythmia.

15. The cardiac stimulator, as set forth in claim 13, wherein the electrical stimulation varies depending upon whether the ventricular tachyarrhythmia is classified as a mild ventricular tachyarrhythmia, a moderate ventricular tachyarrhythmia, or a severe ventricular tachyarrhythmia.

16. The cardiac stimulator, as set forth in claim 13, wherein the algorithm determines the stability of the interval between atrial events and ventricular events by evaluating a plurality of successive intervals between atrial events and ventricular events.

17. The cardiac stimulator, as set forth in claim 16, wherein the algorithm determines the interval between atrial events and ventricular events to be stable if time periods of successive intervals between atrial events and ventricular events do not vary by more than a given amount.

18. The cardiac stimulator, as set forth in claim 13 wherein the algorithm further determines:

if the interval between atrial events and ventricular events is not stable, determining whether the interval between ventricular events is stable;

if the interval between ventricular events is stable, directing the control circuit to direct the pulse generator to deliver electrical stimulation to the ventricle;

if the interval between ventricular events is not stable, withholding treatment of the ventricular tachyarrhythmia.

19. The cardiac stimulator, as set forth in claim 18, further comprising means for comparing a frequency of atrial events with a frequency of ventricular events if the interval between atrial events and ventricular events is not normal;

means for withholding treatment of the ventricular tachyarrhythmia if the frequency of atrial events is greater than the frequency of ventricular events; and means for treating the ventricular tachyarrhythmia if the frequency of atrial events is not greater than the frequency of ventricular events in the given time.

20. The cardiac stimulator, as set forth in claim 19, wherein the control circuit determines that the A–V interval is abnormal if said interval is outside a predetermined range.

21. The cardiac stimulator, as set forth in claim 20, wherein said predetermined range is 85 to 300 milliseconds.

22. The cardiac stimulator, as set forth in claim 19, further comprising means for determining whether the interval between ventricular events is stable if the interval between atrial events and ventricular events is not stable;

means for treating the ventricular tachyarrhythmia if the interval between ventricular events is stable; and means for withholding treatment of the ventricular tachyarrhythmia if the interval between ventricular events is not stable.

23. The cardiac stimulator, as set forth in claim 22, wherein the control circuit determines that the A–V interval is abnormal if said interval is outside a predetermined range.

24. The cardiac stimulator, as set forth in claim 23, wherein said predetermined range is 85 to 300 milliseconds.

25. A cardiac stimulator comprising:

means for determining an interval between ventricular events;

means for determining whether the interval between ventricular events indicates a ventricular tachyarrhythmia;

means for determining whether an interval between atrial events and ventricular events is stable if the interval between ventricular events indicates a ventricular tachyarrhythmia;

means for determining whether the interval between atrial events and ventricular events is normal if the interval between atrial events and ventricular events is stable; and means for withholding treatment of the ventricular tachyarrhythmia if the interval between atrial events and ventricular events is normal.

26. The cardiac stimulator, as set forth in claim 25, wherein the control circuit determines that the A–V interval is abnormal if said interval is outside a predetermined range.

27. The cardiac stimulator, as set forth in claim 26, wherein said predetermined range is 85 to 300 milliseconds.

28. A method of classifying and treating tachyarrhythmias comprising the steps of:

(a) determining an interval between ventricular events;

(b) determining whether the interval between ventricular events indicates a ventricular tachyarrhythmia;

(c) determining whether an interval between atrial events and ventricular events is stable if the interval between ventricular events indicates a ventricular tachyarrhythmia;

(d) determining whether the interval between atrial events and ventricular events is normal if the interval between atrial events and ventricular events is stable; and (e) withholding treatment of the ventricular tachyarrhythmia if the interval between atrial events and ventricular events is normal.

29. The method, as set forth in claim 28, wherein step (c) comprises the step of determining the interval between atrial events and ventricular events to be stable if time periods of successive intervals between atrial events and ventricular events do not vary by more than a given amount.

30. The method, as set forth in claim 29, wherein step (c) comprises the step of evaluating the atrial events to determine whether an atrial event is present between two successive ventricular events to determine the stability of the interval between the atrial events and ventricular events.

31. The method, as set forth in claim 30, wherein step (c) comprises the step of determining the interval between atrial events and ventricular events to be unstable in response to a given number of absences of an atrial event between successive ventricular events.

32. The method, as set forth in claim 28, wherein step (d) comprises determining that the A–V interval is abnormal if said interval is outside a predetermined range.

33. The method, as set forth in claim 32, wherein said predetermined range is 85 to 300 milliseconds.

34. The method, as set forth in claim 28, further comprising the steps of (f) comparing a number of atrial events in a given time with a number of ventricular events in the given time if the interval between atrial events and ventricular events is not normal;

(g) withholding treatment of the ventricular tachyarrhythmia if the number of atrial events in the given time is greater than the number of ventricular events in the given time; and (h) treating the ventricular tachyarrhythmia if the number of atrial events in the given time is not greater than the number of ventricular events in the given time.

35. The method, as set forth in claim 34, wherein step (d) comprises determining that the A–V interval is abnormal if said interval is outside a predetermined range.

36. The cardiac stimulator, as set forth in claim 35, wherein said predetermined range is 85 to 300 milliseconds.

37. The method according to claim 35, further comprising the steps of (i) determining whether the interval between ventricular events is stable if the interval between atrial events and ventricular events is not stable;

(j) treating the ventricular tachyarrhythmia if the interval between ventricular events is stable; and (k) withholding treatment of the ventricular tachyarrhythmia if the interval between ventricular events is not stable.

38. The method, as set forth in claim 37, wherein step (d) further comprises determining that the A–V interval is abnormal if said interval is outside a predetermined range.

39. The method, as set forth in claim 38, wherein said predetermined range is 85 to 300 milliseconds.

* * * * *

UNITED STATES PATENT AND TRADEMARK OFFICE
CERTIFICATE OF CORRECTION

PATENT NO.: 5,873,897

DATED: Feb. 23, 1999

INVENTOR(S): Armstrong et al.

It is certified that errors appear in the above-identified patent and that said patent is hereby corrected as shown below:

In column 9, line 33, delete "polyurethone" and insert -- polyurethane --, therefor.

Signed and Sealed this

Twenty-fourth Day of October, 2000

*Attest:*

Q. TODD DICKINSON

*Attesting Officer*　　*Director of Patents and Trademarks*